United States Patent [19]

Nobles

[11] Patent Number: 5,437,644
[45] Date of Patent: Aug. 1, 1995

[54] METHOD AND APPARATUS FOR REPLACING A CANNULA

[75] Inventor: Anthony A. Nobles, Fountain Valley, Calif.

[73] Assignee: Visioneering, Inc., Fountain Valley, Calif.

[21] Appl. No.: 68,716

[22] Filed: May 26, 1993

[51] Int. Cl.⁶ .................. A61M 5/00; A61M 25/00
[52] U.S. Cl. ................... 604/165; 604/174; 604/164; 604/158
[58] Field of Search ............... 604/264, 272, 280, 158, 604/164, 171, 172; 128/657, 772

[56] References Cited

U.S. PATENT DOCUMENTS

| | | | |
|---|---|---|---|
| 4,498,902 | 2/1985 | Ash | 604/164 |
| 4,581,019 | 4/1986 | Curelaru | 604/164 |
| 4,932,413 | 6/1990 | Shockey | 604/164 |
| 4,969,875 | 11/1990 | Ichikawa | 604/164 |
| 4,994,027 | 2/1991 | Farrell | 604/164 |
| 5,106,376 | 4/1992 | Monnen | 604/158 |
| 5,232,442 | 8/1993 | Johnson | 604/158 |
| 5,275,611 | 1/1994 | Behl | 604/164 |
| 5,281,204 | 1/1994 | Horie | 604/174 |

*Primary Examiner*—C. Fred Rosenbaum
*Assistant Examiner*—Chalin Smith
*Attorney, Agent, or Firm*—Nydegger & Associates

[57] ABSTRACT

A method and an apparatus are disclosed for removal of an existing cannula from a patient and insertion of a replacement cannula into the patient, through the same passageway, by use of a guide rod which maintains the passageway intact. The guide rod is first installed through the existing cannula, and the existing cannula is removed. A hollow trocar, carrying a replacement cannula, is inserted into the patient over the guide rod, then the guide rod and the trocar are removed, leaving the replacement cannula in place in the patient. The guide rod can be fitted with an expandable anchor to hold the guide rod in place during removal of the existing cannula and insertion of the trocar.

16 Claims, 5 Drawing Sheets

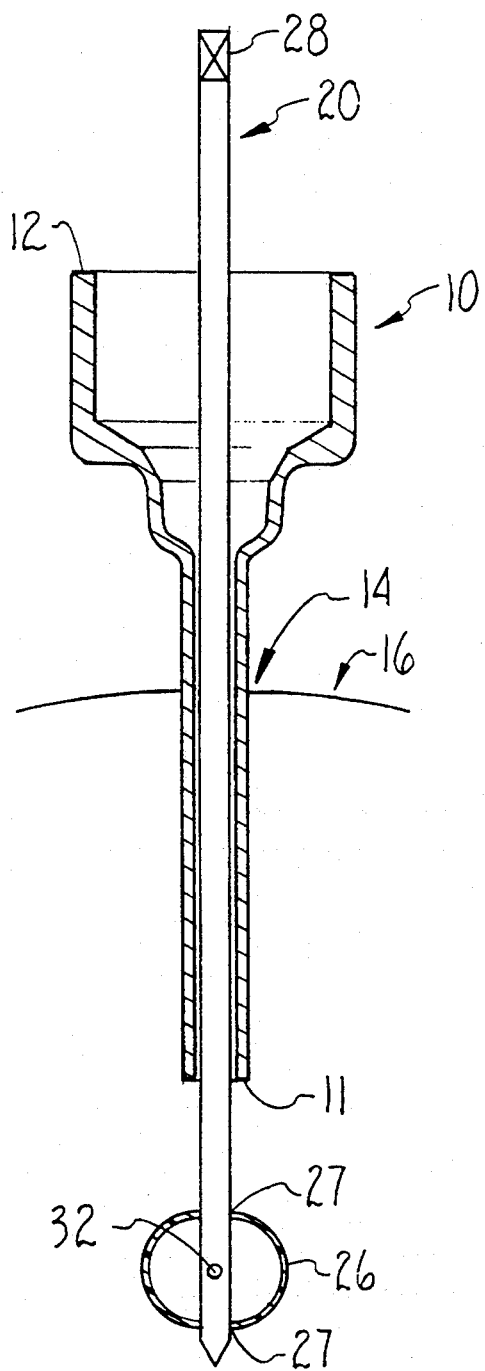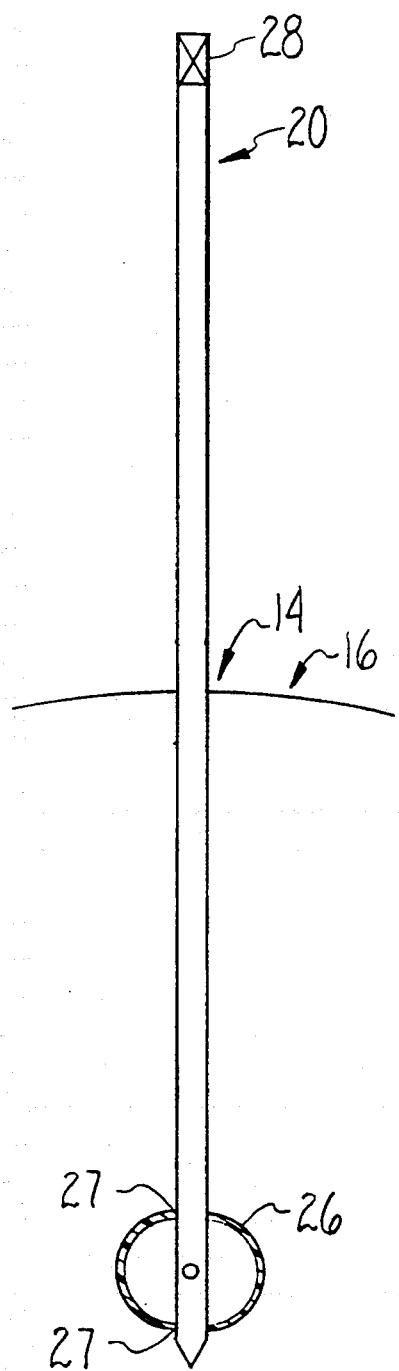

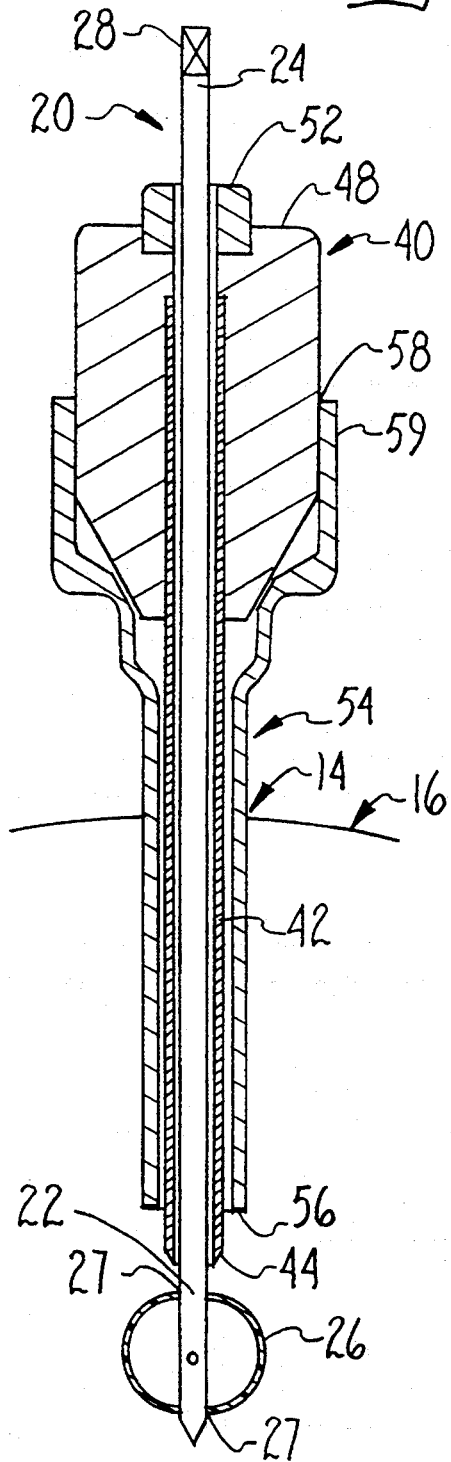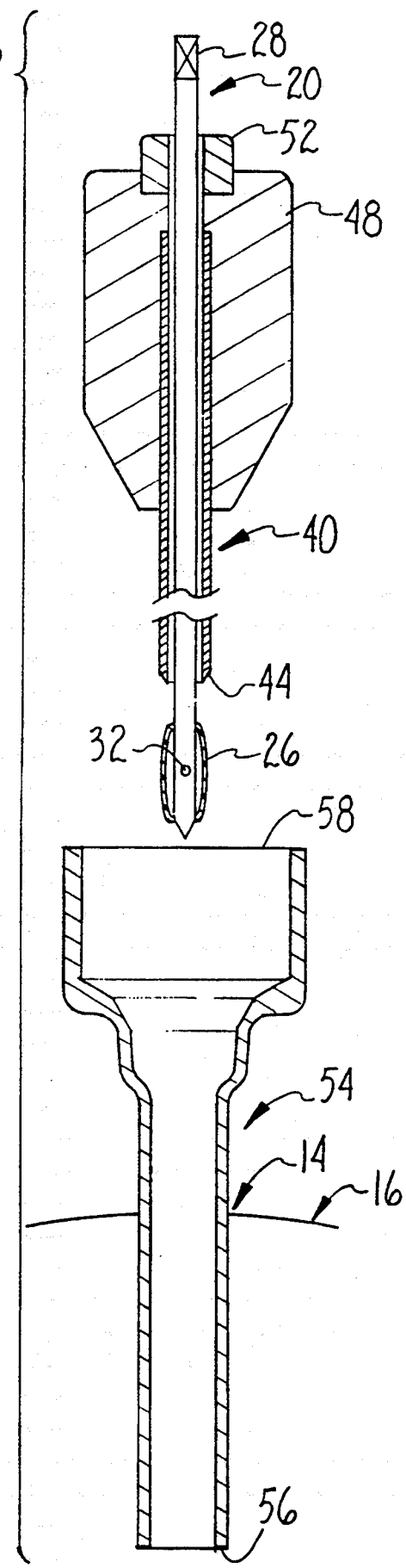

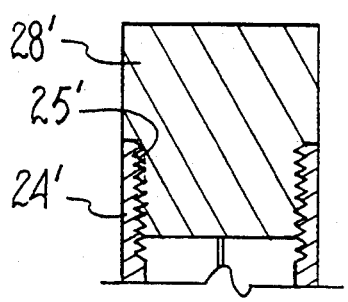
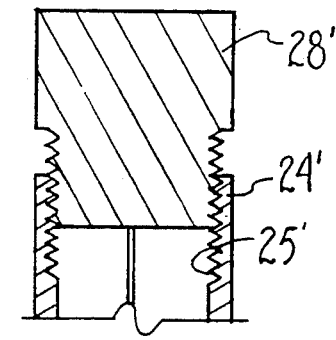
Fig. 10
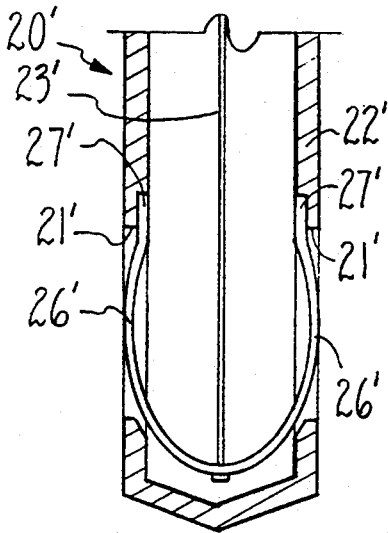
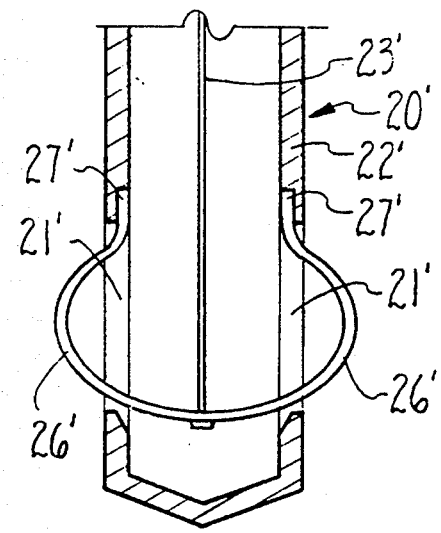
Fig. 11
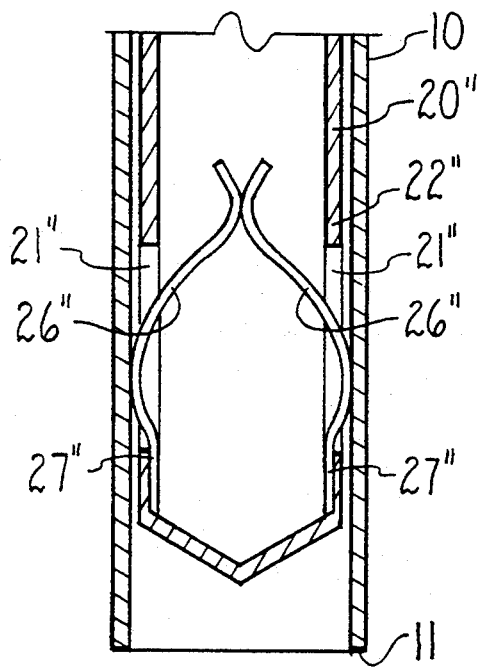
Fig. 12
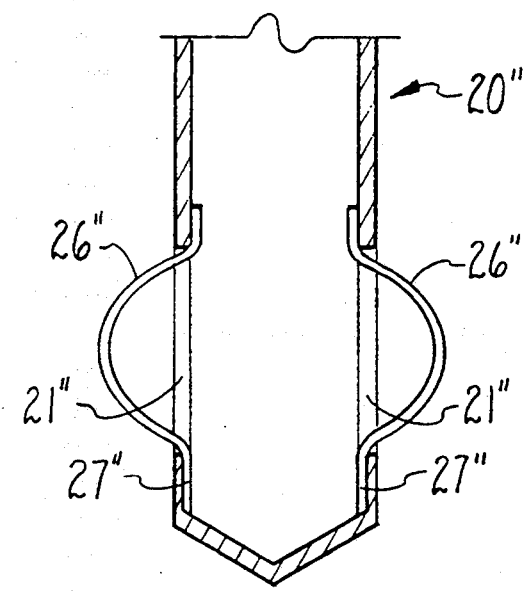
Fig. 13

METHOD AND APPARATUS FOR REPLACING A CANNULA

TECHNICAL FIELD

The present invention relates generally to the field of cannulae used to provide access into internal areas of patients during medical examination or treatment. More specifically, the present invention relates to a method and apparatus useful in removing an existing cannula from a patient and replacing it with a replacement cannula, through the same passageway followed by the first cannula.

BACKGROUND OF THE INVENTION

It is currently known to use a hollow tubular cannula to provide access for a physician to an internal area in a patient. The cannula essentially provides a stable, versatile lumen into the area to be examined or treated. Examination tools, such as endoscopes, can be inserted and withdrawn through the cannula as required. Similarly, surgical instruments or other treatment equipment can be inserted or withdrawn, all without undue trauma to the skin, muscle tissue or other intervening tissue. Cannulae are used for this purpose in order to provide access to the internal area with a minimum of trauma to the intervening tissues, and similarly, the number of cannulae used is held to a minimum.

The means of inserting a cannula is illustrated in FIG. 1, where the cannula 10 is first fitted onto an insertion tool or trocar 13, leaving a sharp point or other cutting contour projecting beyond the distal end 11 of cannula 10. Fitting cannula 10 onto trocar 13 essentially converts them to a single tool for establishing an access passageway into an internal area of the patient 16. The trocar 13 provides the necessary cutting contour and the desired stiffness to facilitate proper insertion of the tools. This is accomplished by inserting the trocar and cannula combination into a puncture 14 in the skin, and continuing on into patient 16 until the distal end 11 of cannula 10 reaches the desired area to be examined or treated.

This insertion process involves the skillful maneuvering of the cutting contour of trocar 13 around and through intervening tissues. The exact path followed will depend not only on the location of puncture 14, but also on the location, configuration, and condition of any intervening tissues. For instance, the path followed through intervening muscle tissue will necessarily pass between certain muscle fibers, depending upon the path chosen by the physician. Insertion of a given cannula at a given location, with a given target, will be able to follow several slightly different paths. After insertion of the trocar 13 and cannula 10, as shown in FIG. 1, trocar 13 is withdrawn from patient 16 through cannula 10, leaving cannula 10 in place in the passageway chosen by the physician, as shown in FIG. 2. Puncture wound 14 in the skin and some of the intervening tissues will, to some extent, close around and conform to cannula 10. Other intervening tissues or organs will, of course, remain clear of the passageway as long as cannula 10 remains in place. Even though examination and treatment via the cannula 10 will minimize trauma to the surrounding tissues, it can be seen that creation of this passageway causes some trauma to the intervening tissues, so creation of additional passageways is to be minimized.

From time to time, it becomes necessary to replace an existing cannula with a different cannula serving the same internal area. This can be required, for example, if the replacement cannula has a larger diameter than the existing cannula, allowing insertion of larger tools, or additional tools, or allowing performance of a different examination or treatment procedure. It is also possible that a replacement cannula might offer other features different from the existing cannula besides diameter. Unfortunately, installation of a replacement cannula in place of an existing cannula currently requires the withdrawal of the existing cannula, followed by insertion of the replacement cannula.

When the existing cannula is withdrawn, the skin and other intervening tissues can close into the established passageway, and internal organs can move into the passageway. This results in the partial or complete disappearance of the passageway, requiring the physician to insert the replacement cannula, with a conventional trocar, into the same puncture. In most cases, the path followed by the insertion of the replacement cannula will not be identical to the path followed by the first cannula. This results in additional trauma to the intervening tissues, accompanied by possible additional postoperative soreness or additional scar tissue. It also requires additional time to withdraw the cannula and to attempt to follow the original passageway with the replacement cannula.

It would be desirable to have a method and apparatus which would allow the replacement of an existing cannula with a different cannula, following the same passageway as that followed by the existing cannula. It is the object of this invention to provide an apparatus which can be inserted through an existing cannula, allowing removal of the cannula and insertion of a trocar along the original passageway. It is a further object of this invention to provide a rod which can be inserted through an existing cannula and anchored in place, allowing removal of the existing cannula over the rod, followed by insertion of a trocar with a new cannula, through the original passageway. It is a further object of this invention to provide a method for inserting a guide rod through an existing cannula, anchoring the rod in place, removing the existing cannula, and insertion of a replacement cannula through the original passageway. Finally, it is an object of this invention to provide a method and apparatus for replacement of a cannula, which are relatively cost effective and easy to operate.

SUMMARY OF THE INVENTION

The present invention provides a method and apparatus for withdrawal of an existing cannula from a patient and replacement with a different cannula, which can be of a larger size. The preferred embodiment of the invention typically provides a rigid elongated guide rod which has an anchor device mounted on its distal end. The anchor device can be an inflatable balloon or some other expandable device. The guide rod has a sufficiently small diameter to allow the existing cannula to be withdrawn from the patient over the proximal end of the guide rod. The invention also provides a hollow trocar which can slide over the guide rod into the patient, with a replacement cannula affixed to the trocar in the normal fashion. The hollow trocar has a cutting edge on its distal end, so that it is capable of opening the existing entry puncture and passageway wider, to allow entry of the replacement cannula.

The invention also provides a method of use of the new apparatus, beginning with insertion of the guide rod into the existing cannula, until the distal end of the guide rod extends beyond the distal end of the existing cannula. The anchor balloon on the distal end of the guide rod is then inflated, and any inflation tubing removed. The existing cannula is then withdrawn from the patient, over the guide rod proximal end. Then, the hollow trocar is fitted with a replacement cannula and inserted into the patient, over the guide rod. Next, the anchor balloon is deflated. Finally, the guide rod and the hollow trocar are withdrawn from the replacement cannula, which is left in place in the original passageway in the patient.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 6 is a sectional view of the guide rod of FIG. 1 with its anchor balloon inflated;

FIG. 7 is a sectional view of the guide rod of FIG. 1 remaining in the patient after withdrawal of the existing cannula;

FIG. 8 is a sectional view of the hollow trocar and replacement cannula of FIG. 4 inserted into the patient over the guide rod of FIG. 1;

FIG. 9 is a sectional view of the guide rod and the hollow trocar withdrawn from the replacement cannula, leaving the cannula in the patient;

FIG. 10 is a sectional view of an alternate embodiment of the anchor device mounted on the distal end of the guide rod, in the retracted condition;

FIG. 11 is a sectional view of the anchor device of FIG. 10, in the expanded condition;

FIG. 12 is a sectional view of a second alternative embodiment of the anchor device, in the retracted condition; and FIG. 13 is a sectional view of the anchor device of FIG. 12, in the expanded condition.

DESCRIPTION OF PREFERRED EMBODIMENTS

Figure 1:
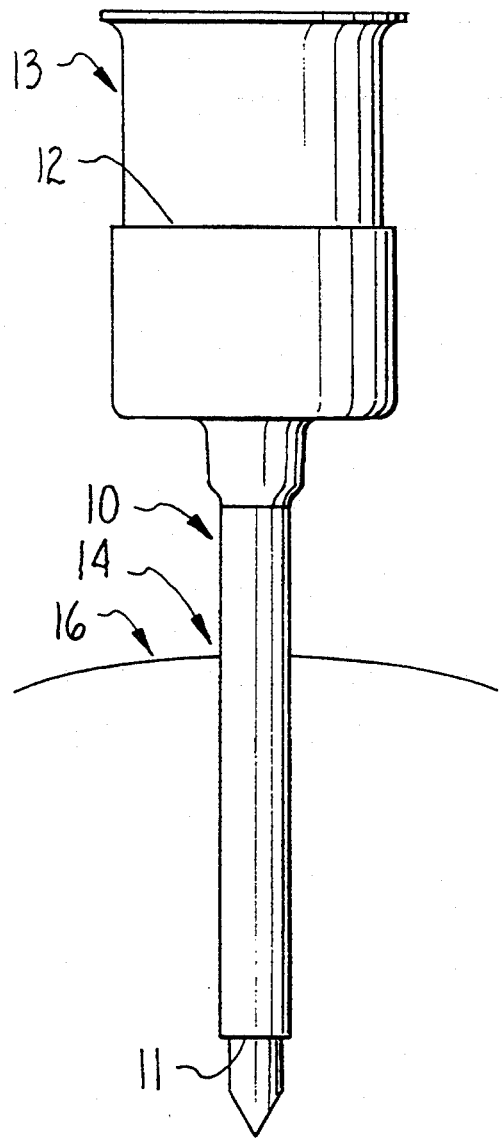
FIG. 1 is an elevation view of a cannula mounted on a trocar, inserted into a patient, as is known in the art.
Figure 2:
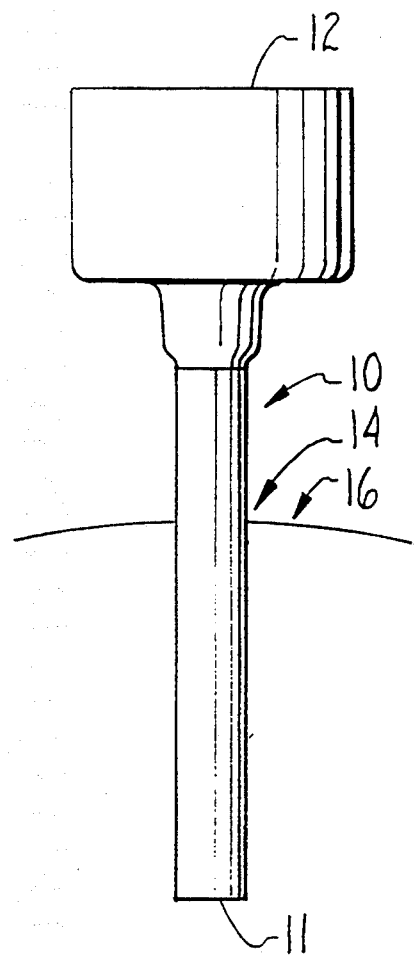
FIG. 2 is an elevation view of the cannula of FIG. 1, left in the patient, after withdrawal of the trocar, as is known in the art.

As seen in FIG. 1, it is known in the art to insert a hollow cannula 10 into a patient 16 by first inserting a trocar 13 through cannula 10, extending from proximal end 12 through distal end 11 of cannula 10. The trocar 13 and cannula 10 are then inserted through puncture 14 into the intended treatment area in patient 16. Trocar 13 is then withdrawn, leaving cannula 10 in place in the patient 16, as shown in FIG. 2. Hollow cannula 10 then provides an opening for examination or treatment of patient 16, with instruments being inserted through proximal end 12 and extending beyond distal end 11.

Figure 3:
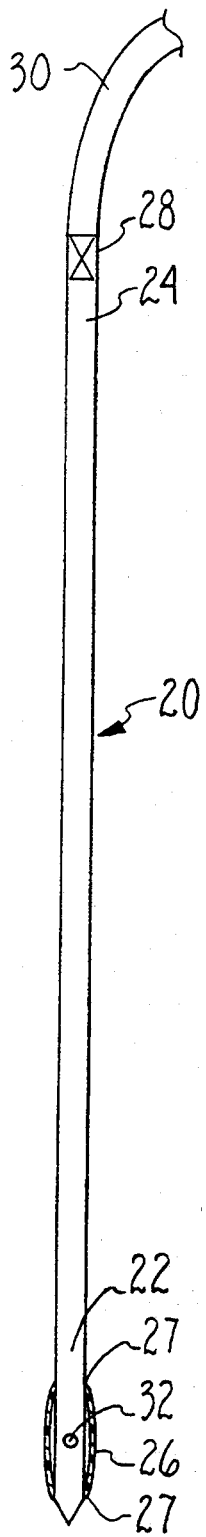
FIG. 3 is a sectional view of a guide rod of the present invention.

FIG. 3 shows rigid, elongated, tubular guide rod 20 of the present invention, as it would look prior to insertion into the patient. Mounted on the distal end 22 of guide rod 20 is inflatable anchor balloon 26, shown in the deflated condition. Other anchor devices can be used instead of anchor balloon 26, as long as they extend somewhat transversely from guide rod 20, like anchor balloon 26, and as long as they are expandable. Two alternative anchor devices will be described later. Anchor balloon 26 is securely fastened to guide rod 20 at attachment sites 27, one at each end of anchor balloon 26. Attachment sites 27 also are fluid tight, to facilitate the inflation of anchor balloon 26.

Mounted on the proximal end 24 of guide rod 26 is locking valve 28. Locking valve 28 is sized so as to pass through the internal bore of cannula 10, as will be explained later. Locking valve 28 can be an in-line valve as is known in the art, which can allow the flow of fluid in either direction, and which can be closed to block flow. Attached to locking valve 28 is fluid supply line 30, which can be detached as desired during performance of the method of the present invention. Fluid supply line 30 provides an inflation fluid via locking valve 28, down through guide rod 20, out inflation port 32, and into anchor balloon 26. After inflation of anchor balloon 26, locking valve 28 can be shut and supply line 30 removed, leaving anchor balloon 26 locked in the inflated condition. Alternatively, a small canister of compressed fluid can be used in place of supply line 30, and the canister can be left in place, if it has a small enough diameter to pass through the existing cannula. When desired, locking valve 28 can be opened to deflate anchor balloon 26. If an alternative anchor device is used, which does not expand by inflation, another suitable locking device can be substituted for locking valve 28.

Figure 4:
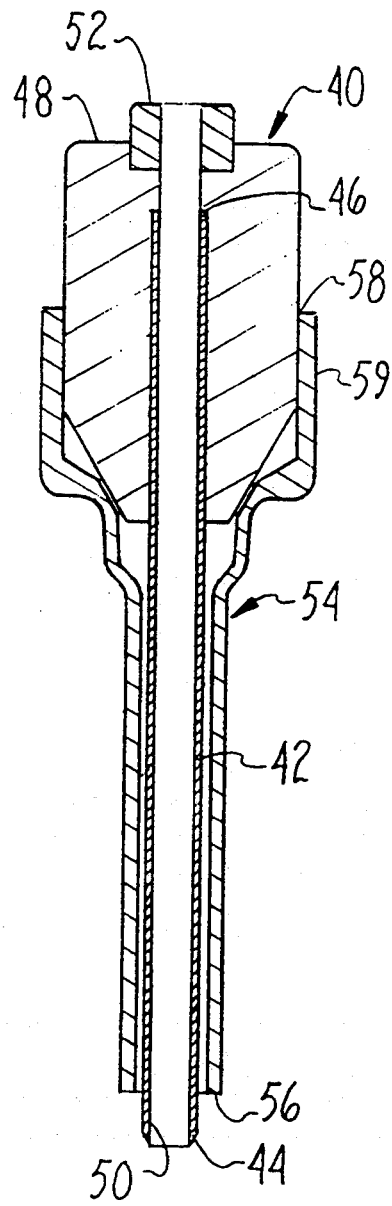
FIG. 4 is a sectional view of a hollow trocar and replacement cannula of the present invention.

FIG. 4 shows hollow exchange trocar 40 according to the present invention, inserted through replacement cannula 54. Replacement cannula 54 has a handle 59 near its proximal end 58, and a tubular body terminating at distal end 56. Replacement cannula 54 can have a larger diameter than existing cannula 10, or it may have some other feature which the attending physician requires. Exchange trocar 40 has a handle 48 attached to the proximal end 46 of its tubular piercing element 42. A cutting contour is formed on the distal end 44 of piercing element 42, which extends beyond the distal end 56 of replacement cannula 54.

The inner diameter 50 of a hollow bore through exchange trocar 40 is sized to allow the passage of guide rod 20 and anchor balloon 26. Locknut 52 is a typical device for gripping guide rod 20, such as with a split collet (not shown). If desired, spring loaded slips could be used, or a force fit nylon fitting could serve, to retain guide rod 20, or no gripping device at all could be used. The fit between exchange trocar 40 and replacement cannula 54 is a slip fit, with trocar 40 providing the necessary cutting contour and rigidity to penetrate tissues upon insertion into a patient.

OPERATION

Figure 5:
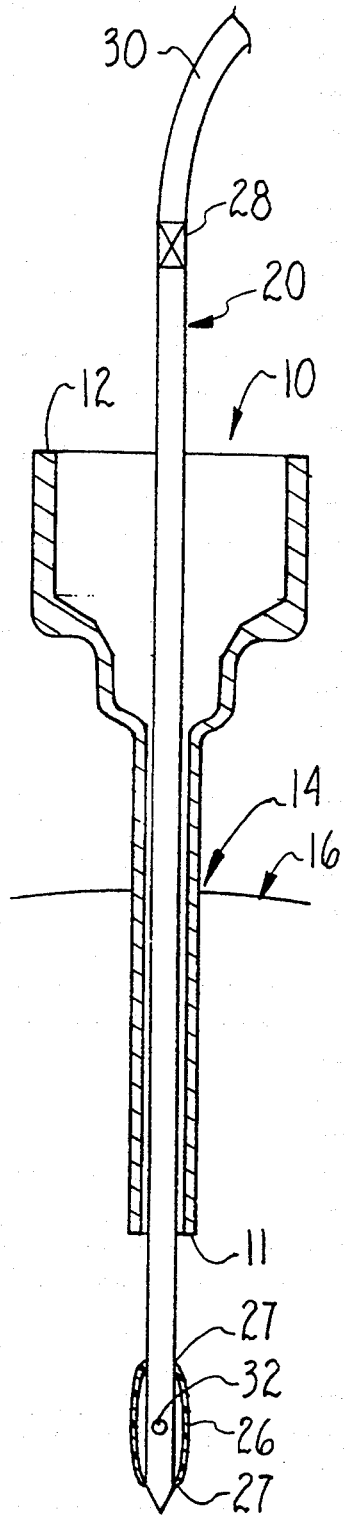
FIG. 5 is a sectional view of the guide rod of FIG. 1 inserted into an existing cannula in a patient.

The method of operation of the apparatus of the present invention will now be described. As seen in FIG. 5, if it is desired to replace existing cannula 10 with a different, possibly larger cannula, guide rod 20 is attached to a fluid supply 30, and, with anchor balloon 26 deflated, guide rod 20 is inserted into patient 16 through existing cannula 10. Guide rod 20 is inserted until its distal end 22 extends beyond the distal end 11 of existing cannula 10.

As seen in FIG. 6, guide rod 20 is then anchored in place in the patient by inflation of anchor balloon 26, by applying fluid pressure from supply line 30, down through guide rod 20, and out port 32. Locking valve 28 is then shut, locking anchor balloon 26 in the inflated condition, anchoring guide rod 20 in place by contact with surrounding tissues internally in the patient. Then, supply line 30 can be removed.

FIG. 7 shows guide rod 20 anchored in place in patient 16, after withdrawal of existing cannula 10. In this condition, guide rod 20 will maintain the original passageway into the treatment area of patient 16, as established by the physician upon initial insertion of cannula 10 and trocar 13. Guide rod 20 can not easily withdraw from puncture 14, because anchor balloon 26 has expanded behind the intervening tissues between puncture 14 and the treatment area.

While guide rod 20 maintains the original passageway, exchange trocar 40, fitted with replacement cannula 54, is inserted into patient 16 over guide rod 20, as shown in FIG. 8. If required, the cutting contour on the distal end 44 of exchange trocar 40 enlarges puncture 14 and the existing passageway along guide rod 20. As shown in FIG. 9, anchor balloon 26 is then deflated, and guide rod 20 and exchange trocar 40 are withdrawn, leaving replacement cannula 54 in place.

ALTERNATIVE EMBODIMENTS AND THEIR OPERATION

As seen in FIG. 10, instead of an anchor balloon, guide rod 20' can have a transversely extending anchor basket 26' attached to guide rod 20' at attachment points 27', and extendable through vertical slots 21'. Anchor basket 26' is constructed of flexible legs attached to guide rod 20' at points 27' and attached to basket flex wire 23' which is attached to threaded locking nut 28'. When desired, locking nut 28' is screwed out of guide rod 20' by the interaction of threads 25' pulling on flex wire 23' and flexing anchor basket 26' to the shape shown in FIG. 11. As shown in FIG. 11, the legs of basket 26' extend through slots 21' to extend transversely to guide rod 20'.

As seen in FIG. 12, another embodiment of the anchor device has flexible anchor arms 26" attached to guide rod 20" at attachment points 27". When anchor arms 26" are not constrained by a trocar or cannula, as shown in FIG. 13, they automatically extend through slots 21" to extend transversely to guide rod 20".

While the particular method and apparatus for replacement of a cannula as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

I claim:

1. A method for installing a replacement cannula in place of an existing cannula in a patient, comprising the steps of:
   inserting a guide rod into a hollow bore in the existing cannula in the patient;
   withdrawing the existing cannula from the patient, over a proximal end of said guide rod;
   mounting a replacement cannula concentrically on the exterior of a hollow trocar;
   sliding said hollow trocar and said replacement cannula concentrically over said proximal end of said guide rod into the patient; and
   withdrawing said guide rod and said hollow trocar from the patient through said replacement cannula.

2. A method for installing a replacement cannula, as claimed in claim 1, wherein said replacement cannula is larger in diameter than the existing cannula.

3. A method for installing a replacement cannula, as claimed in claim 1, wherein said guide rod is inserted into the existing cannula to a sufficient depth to extend a distal end of said guide rod beyond a distal end of the existing cannula.

4. A method for installing a replacement cannula, as claimed in claim 3, further comprising the step of selectively expanding an expandable anchor means mounted on said distal end of said guide rod, to anchor said distal end of said guide rod in place in the patient.

5. A method for installing a replacement cannula in place of an existing cannula in a patient, comprising the steps of:
   inserting an elongated, rigid guide rod into a hollow bore in the existing cannula in the patient, to a sufficient depth to expose a distal end of said guide rod beyond the distal end of the existing cannula;
   inflating an anchor balloon mounted on said distal end of said guide rod, to anchor said distal end of said guide rod in place in the patient;
   withdrawing the existing cannula from the patient over a proximal end of said guide rod;
   mounting a replacement cannula concentrically on the exterior of a hollow, rigid trocar;
   sliding said trocar and said replacement cannula concentrically over said proximal end of said guide rod into the patient;
   deflating said anchor balloon; and
   withdrawing said guide rod and said trocar from the patient through said replacement cannula.

6. A method for installing a replacement cannula, as claimed in claim 5, wherein said replacement cannula is larger in diameter than the existing cannula.

7. An apparatus for installing a cannula in place of an existing cannula in a patient, comprising:
   an existing cannula, said existing cannula having a hollow bore;
   an elongated guide rod insertable through said hollow bore in said existing cannula;
   a selectively inflatable balloon mounted on a distal end of said guide rod for anchoring said distal end of said guide rod in place in the patient; and
   a hollow trocar sized to slide concentrically over a proximal end of said guide rod into the patient.

8. An apparatus for installing a cannula, as claimed in claim 7, wherein said guide rod is configured to allow said existing cannula to be withdrawn over said proximal end of said guide rod.

9. An apparatus for installing a cannula, as claimed in claim 7, wherein said guide rod has sufficient length to allow a distal end of said guide rod to extend beyond a distal end of said existing cannula while said proximal end of said guide rod remains projecting from a proximal end of said existing cannula.

10. An apparatus for installing a cannula, as claimed in claim 7, wherein said guide rod is rigid.

11. An apparatus for installing a cannula, as claimed in claim 7, further comprising expansion means for selectively expanding and retracting said balloon.

12. An apparatus for installing a cannula, as claimed in claim 11, further comprising locking means for selectively locking said expansion means in expanded and retracted conditions.

13. An apparatus for installing a cannula, as claimed in claim 7, further comprising a replacement cannula concentrically mountable on said trocar for insertion over said guide rod into the patient.

14. An apparatus for installing a cannula, as claimed in claim 13, wherein said replacement cannula is larger in diameter than the existing cannula.

15. An apparatus for installing a replacement cannula in place of an existing cannula in a patient, comprising:
- an existing cannula, said existing cannula having a hollow bore;
- an elongated, rigid guide rod insertable through said hollow bore in said existing cannula, with a distal end of said guide rod extending beyond a distal end of said existing cannula;
- an inflatable anchor balloon mounted on a distal end of said guide rod for anchoring said distal end of said guide rod in place in the patient;
- inflation means for selectively inflating and deflating said anchor balloon;
- a hollow, rigid trocar sized to slide concentrically over a proximal end of said guide rod into the patient, after withdrawal of said existing cannula; and
- a replacement cannula concentrically mountable on said trocar for insertion over said guide rod, with said trocar, into the patient.

16. An apparatus for installing a replacement cannula, as claimed in claim 15, wherein said replacement cannula is larger in diameter than said existing cannula.

* * * * *